United States Patent
Shih et al.

(10) Patent No.: US 9,556,436 B2
(45) Date of Patent: Jan. 31, 2017

(54) METHOD OF TREATING INFLUENZA A

(71) Applicant: Chang Gung University, Taoyuan (TW)

(72) Inventors: Shin-Ru Shih, Taoyuan (TW); Chi-Jene Chen, Taoyuan (TW); Sheng-Yu Huang, Taoyuan (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 0 days.

(21) Appl. No.: 14/747,041

(22) Filed: Jun. 23, 2015

(65) Prior Publication Data

US 2016/0376597 A1 Dec. 29, 2016

(51) Int. Cl.
*C12N 15/11* (2006.01)
*C12N 15/113* (2010.01)
*C12Q 1/70* (2006.01)

(52) U.S. Cl.
CPC ........... *C12N 15/1131* (2013.01); *C12Q 1/701* (2013.01); *C12N 2310/141* (2013.01); *C12N 2310/315* (2013.01); *C12N 2310/321* (2013.01); *C12N 2320/30* (2013.01); *C12Q 2600/158* (2013.01); *C12Q 2600/178* (2013.01)

(58) Field of Classification Search
CPC ...................... C12N 2310/141; C12N 15/1131
See application file for complete search history.

(56) References Cited

PUBLICATIONS

Wei Wu, Thesis:Unveiling the neglected roles of nucleoprotein NLS2 and cellular vimentin during Influenza A virus infection, Dec. 2014 The University of British Columbia, pp. 1-232.*
Transmission of Influenza Viruses from Animals to People, http://www.cdc.gov/flu/about/viruses/transmission.htm, retrieved on Jun. 9, 2016, pp. 1-4.*
Barnes et al. Cell Host & Microbe 4, 239-248, 2008.*

* cited by examiner

*Primary Examiner* — Brian Whiteman
(74) *Attorney, Agent, or Firm* — Volpe and Koenig, P.C.

(57) ABSTRACT

A method of treating Influenza A is disclosed. The method includes the step of administering a pharmaceutical composition including an oligonucleotide complementary to a corresponding segment of the nucleotide sequence of micro-RNA-1290 (miR-1290) (SEQ ID NO: 1) to a subject suffering from Influenza A, wherein at least one of the nucleotides in the oligonucleotide is Thymidine phosphate.

15 Claims, 19 Drawing Sheets

SEQUENCE LISTING

```
<160> NUMBER OF SEQ ID NOS: 2

<210> SEQ ID NO 1
<211> LENGTH: 19
<212> TYPE: RNA
<213> ORGANISM: Homo sapiens

<400> SEQUENCE: 1
uggauuuuug gaucaggga                                                19

<210> SEQ ID NO 2
<211> LENGTH: 19
<212> TYPE: DNA
<213> ORGANISM: Artificial Sequence
<220> FEATURE:
<223> OTHER INFORMATION: complementary to the nucleotide sequence of
```

-continued

```
      miR-1290

<400> SEQUENCE: 2
tccctgatcc aaaaatcca                                              19
```

METHOD OF TREATING INFLUENZA A

FIELD OF THE INVENTION

The present invention relates to a method of treating Influenza, and more particularly to a method of treating Influenza A.

BACKGROUND OF THE INVENTION

Influenza A virus is a virus with high morbidity, high mortality and high contagion. Influenza A virus can use birds or pigs as reservoir hosts in order to continuously spread and exist among different species, produce antigenic shifts through genetic reassortment, and overcome the species barrier to infect humans. Moreover, antigenic drifts caused by quick and unpredictable mutations of the influenza A virus causes people who have been infected with the influenza A virus to be infected again. Because of these two antigenic evolutionary mechanisms, an epidemic or pandemic influenza occurs every few years or decades. Millions of people are infected every year, causing a tremendous burden to health and the economy.

A microRNA (abbreviated miRNA) is a small RNA molecule containing about 22 nucleotides. After transcription, a primary miRNA (pri-miRNA) is cleaved by RNase III enzyme Drosha in the nucleus, and RNase III enzyme Drosha can cleave the double stranded pri-miRNA near the stem-loop and produce a precursor-miRNA (pre-miRNA) having a stem-loop structure and 60-70 nucleotides. Pre-miRNA is exported out of the nucleus by Exportin-5. In the cytoplasm, the pre-miRNA hairpin is cleaved by the RNase III enzyme Dicer, yielding a miRNA:miRNA* duplex about 22 nucleotides in length, and one strand of the miRNA:miRNA* duplex is incorporated into the RNA-induced silencing complex (RISC). The function of the RISC is protein translation inhibition.

In recent years, substantial literature has indicated that miRNA can regulate viral replication. However, whether there exists a species-specific miRNA which can regulate influenza A viral replication remains unknown.

SUMMARY OF THE INVENTION

In accordance with one aspect of the present invention, a method of diagnosing Influenza A is disclosed. The method includes the step of determining a level of microRNA-1290 (miR-1290) in a cell of a subject based on a measurement of a level of an oligonucleotide complementary to a corresponding segment of the nucleotide sequence of miR-1290 (SEQ ID NO: 1), wherein at least one of the nucleotides in the oligonucleotide is Thymidine phosphate.

In accordance with another aspect of the present invention, a method of treating Influenza A is disclosed. The method includes the step of administering a pharmaceutical composition including an oligonucleotide complementary to a corresponding segment of the nucleotide sequence of microRNA-1290 (miR-1290) (SEQ ID NO: 1) to a subject suffering from Influenza A, wherein at least one of the nucleotides in the oligonucleotide is Thymidine phosphate.

In accordance with a further aspect of the present invention, a method of treating Influenza A is disclosed. The method includes the step of administering a pharmaceutical composition including an oligonucleotide complementary to a corresponding segment of the nucleotide sequence of microRNA-1290 (miR-1290) (SEQ ID NO: 1) to a subject suffering from Influenza A.

The above objects and advantages of the present invention will become more readily apparent to those ordinarily skilled in the art after reviewing the following detailed descriptions and accompanying drawings, in which:

DETAILED DESCRIPTION OF THE PREFERRED EMBODIMENTS

Figure 1A:
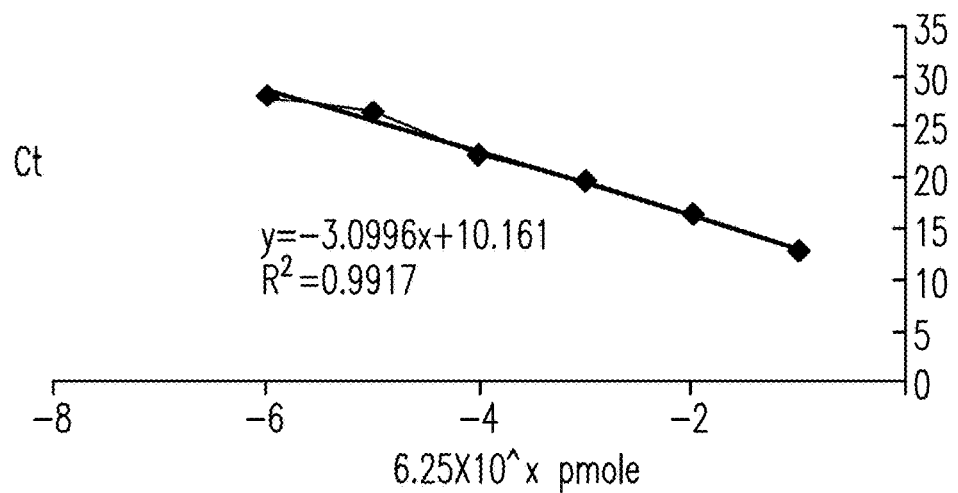
FIG. 1(a) shows the Ct-number equation obtained by real-time polymerase chain reaction (real-time PCR) through serial dilution of pre-miR-1290 (Ambion, Pre-miR™ miRNA Starter Kit)
Figure 1B:
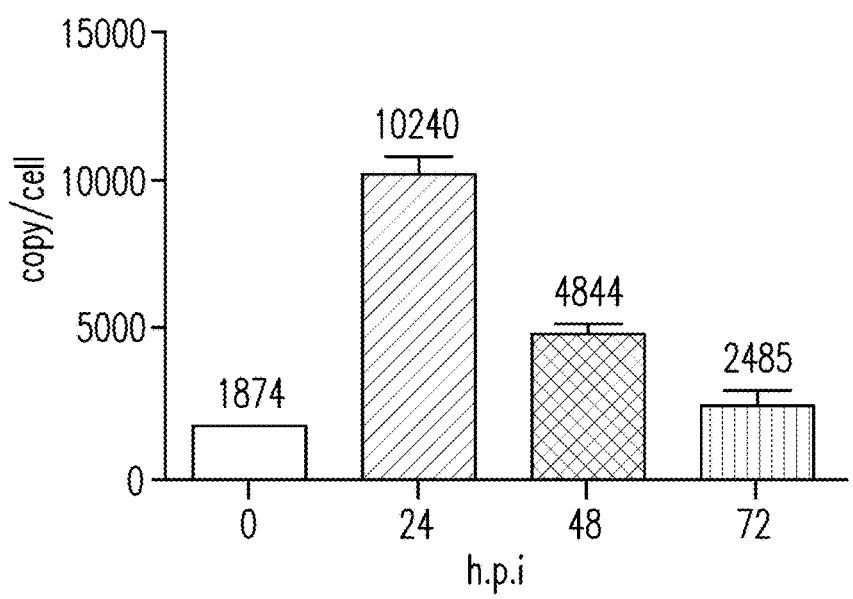
FIG. 1(b) shows the verification of expression levels of the screened miRNA Homo sapiens miRNA-1290 (hsa-miR-1290) after A/WSN/33 (H1N1) multiple infection by real-time polymerase chain reaction (real-time PCR)
Figure 1C:
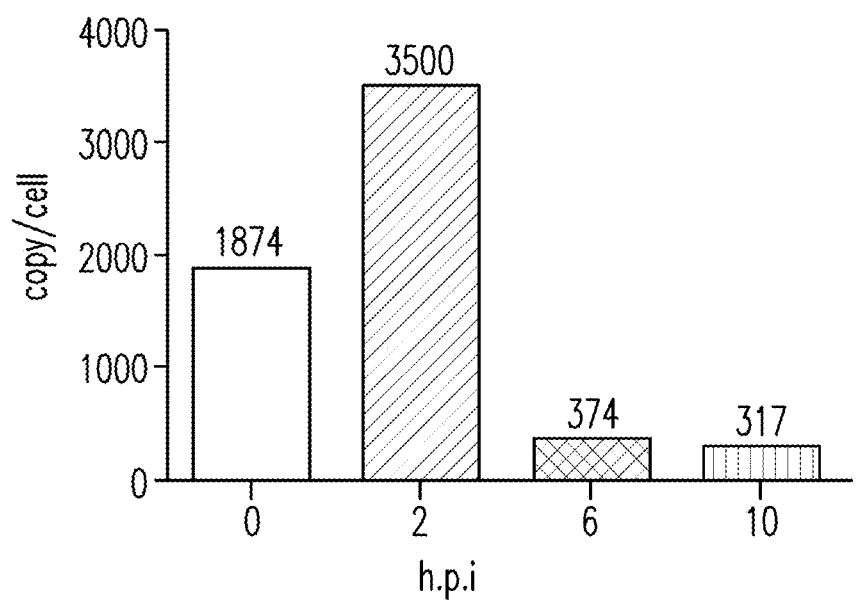
FIG. 1(c) shows the verification of expression levels of the screened miRNA hsa-miR-1290 after A/WSN/33 (H1N1) single infection by real-time polymerase chain reaction (real-time PCR)
Figure 2A:
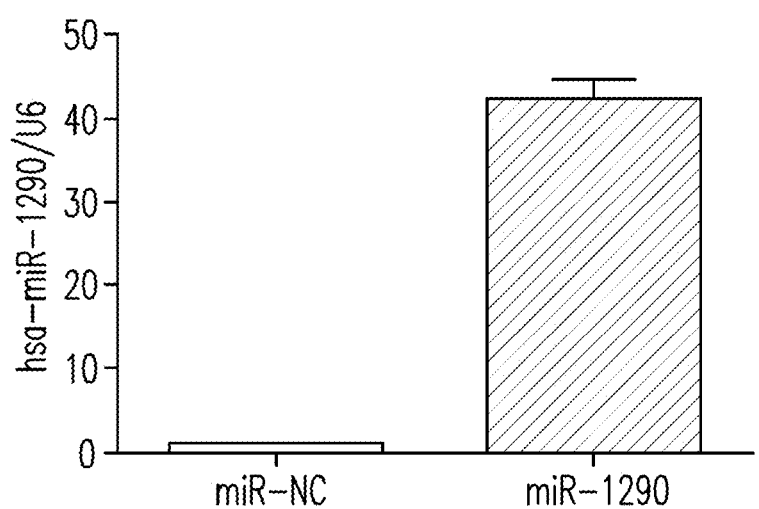
FIG. 2(a) shows the transfection efficiency of hsa-miR-1290 in A549 cells.
Figure 2B:
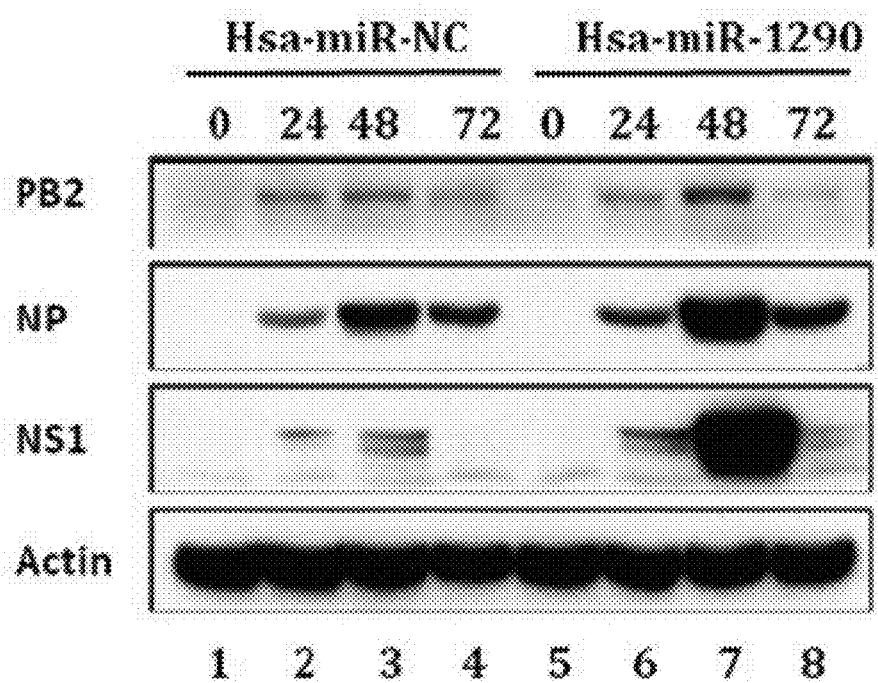
FIG. 2(b) shows the viral protein expression in A549 cells transfected with hsa-miR-1290 after A/WSN/33 (H1N1) multiple infection.
Figure 2C:
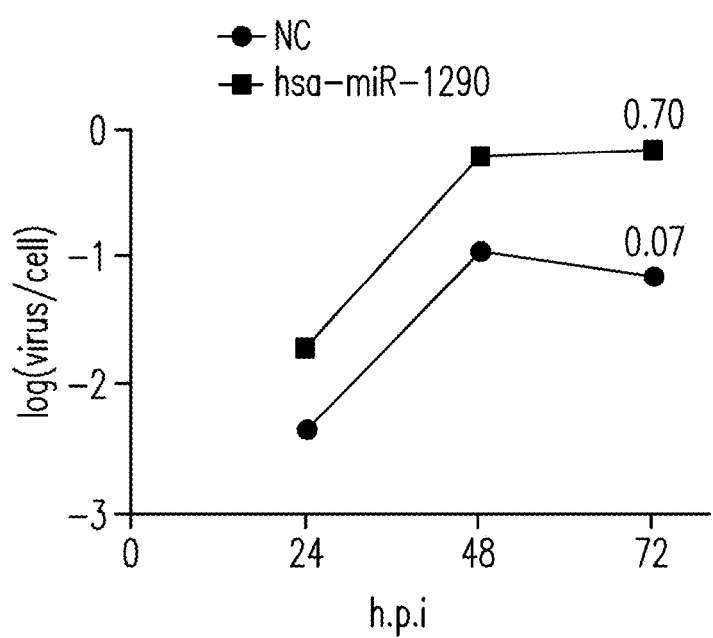
FIG. 2(c) shows the viral production of a single cell transfected with hsa-miR-1290 after A/WSN/33 (H1N1) multiple infection.
Figure 3A:
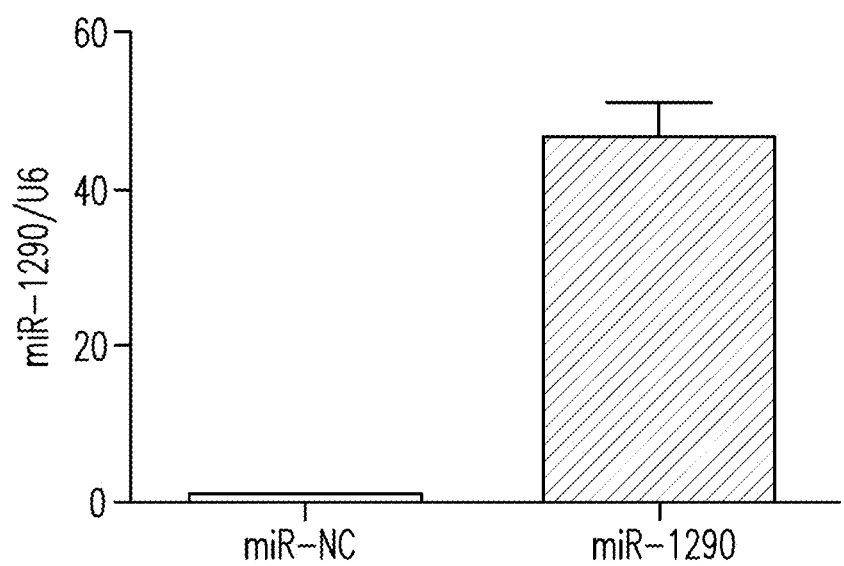
FIG. 3(a) shows the transfection efficiency of hsa-miR-1290 in A549 cells.
Figure 3B:
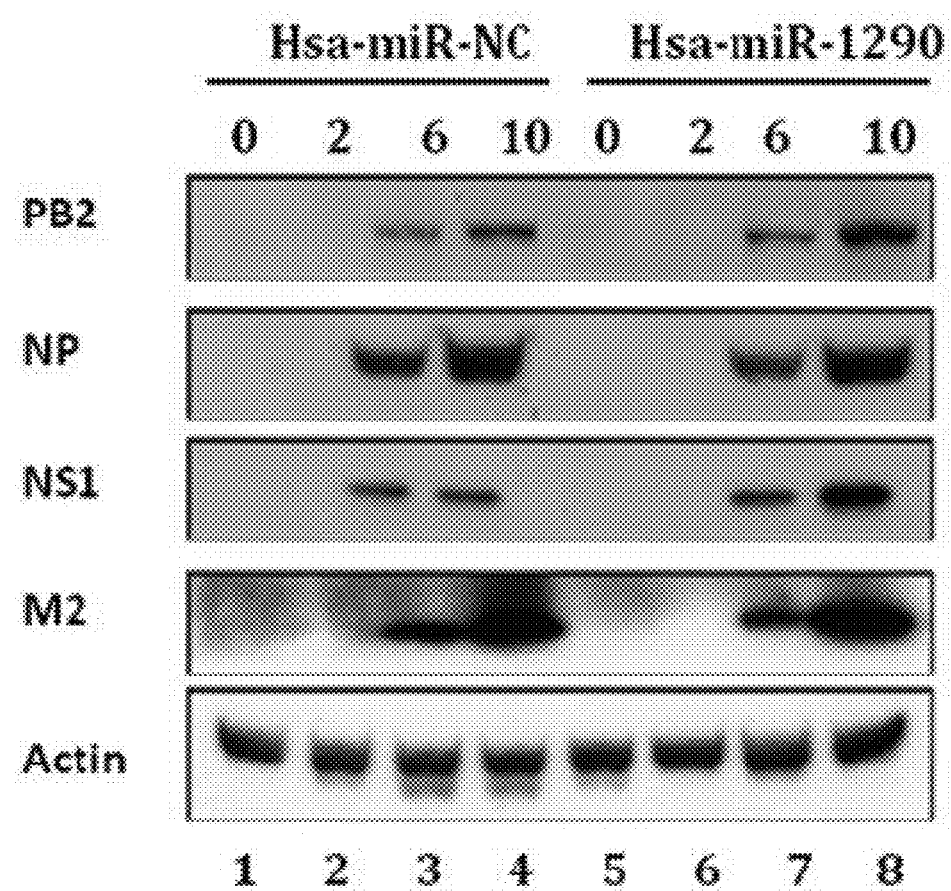
FIG. 3(b) shows the viral protein expression in A549 cells transfected with hsa-miR-1290 after A/WSN/33 (H1N1) single infection.
Figure 3C:
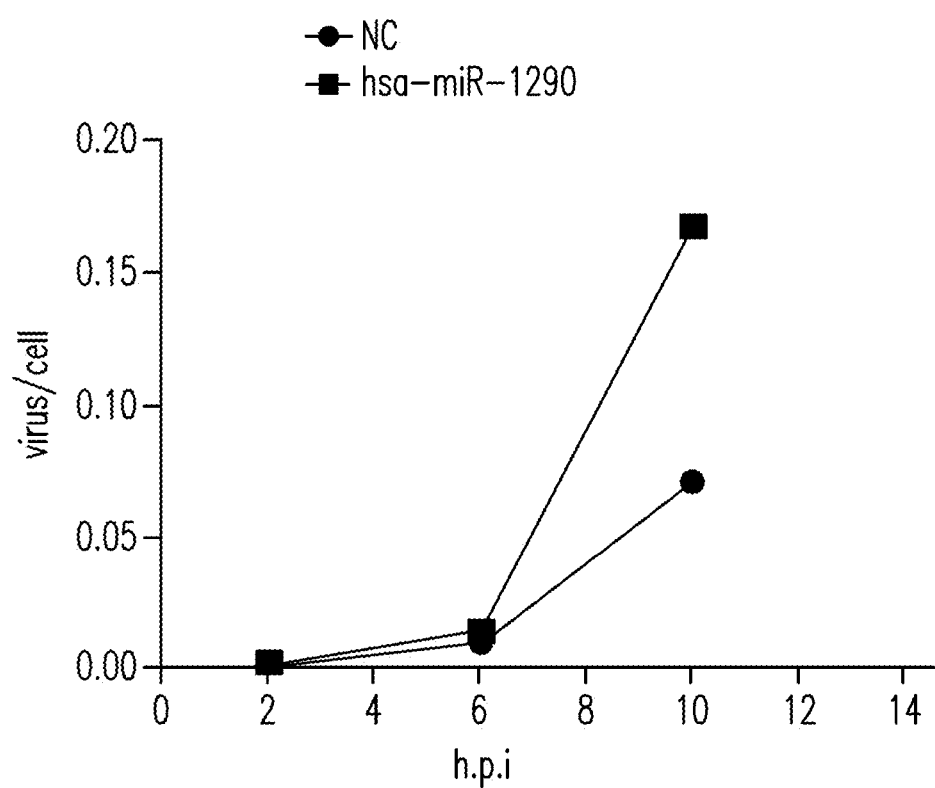
FIG. 3(c) shows the viral production of a single cell transfected with hsa-miR-1290 after A/WSN/33 (H1N1) single infection.
Figure 4A:
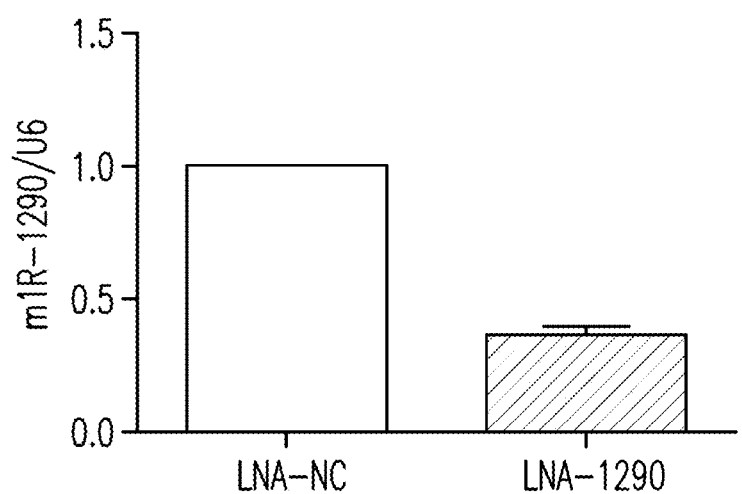
FIG. 4(a) shows the transfection efficiency of locked nucleic acid miRNA 1290 (LNA-1290) in A549 cells.
Figure 4B:
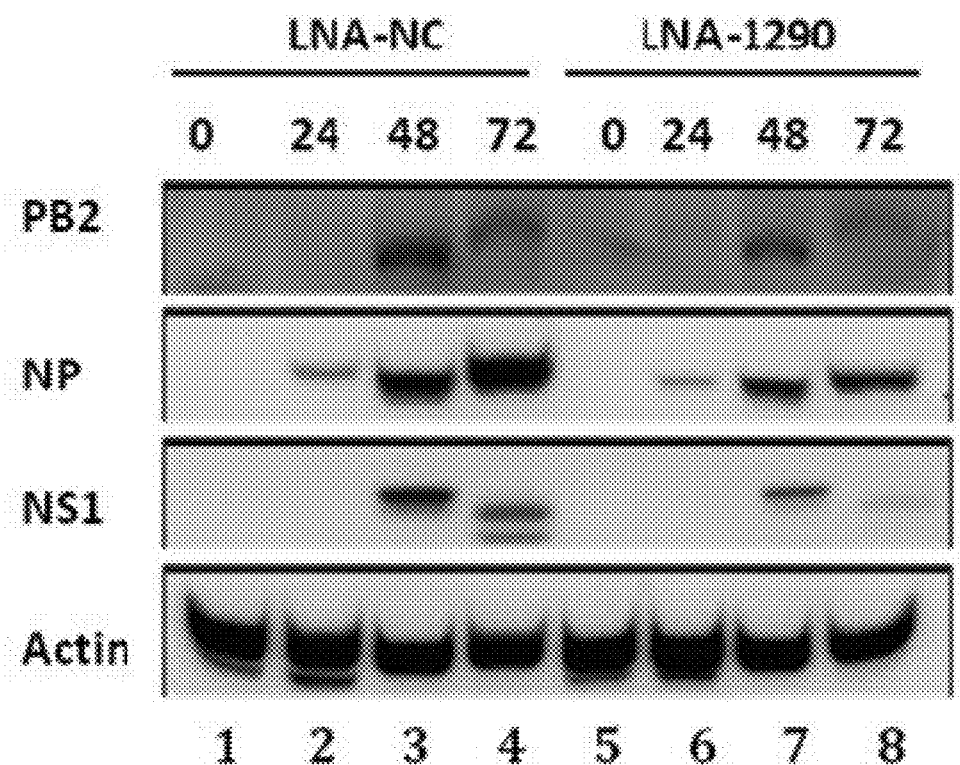
FIG. 4(b) shows the viral protein expression in A549 cells transfected with LNA-1290 after A/WSN/33 (H1N1) multiple infection.
Figure 4C:
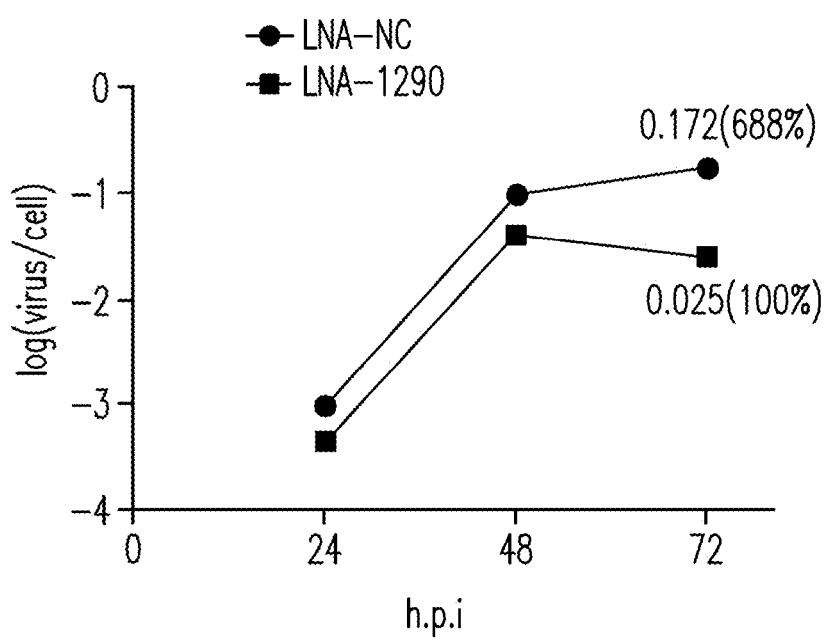
FIG. 4(c) shows the viral production of a single cell transfected with LNA-1290 after A/WSN/33 (H1N1) multiple infection.
Figure 5A:
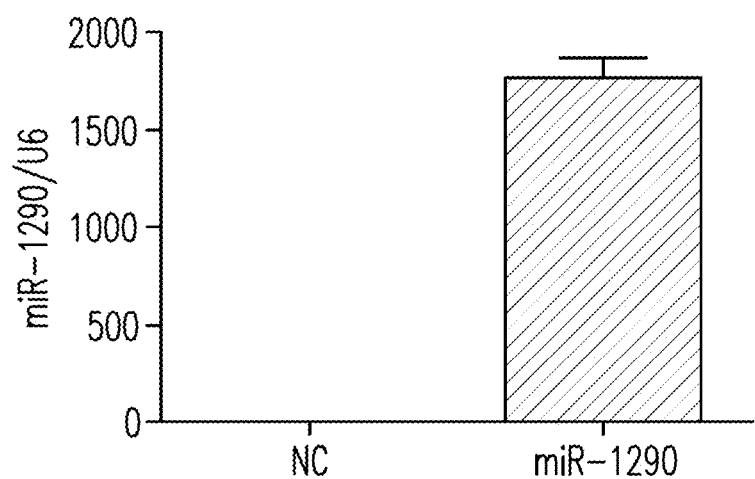
FIG. 5(a) shows the transfection efficiency of hsa-miR-1290 in A549 cells.
Figure 5B:
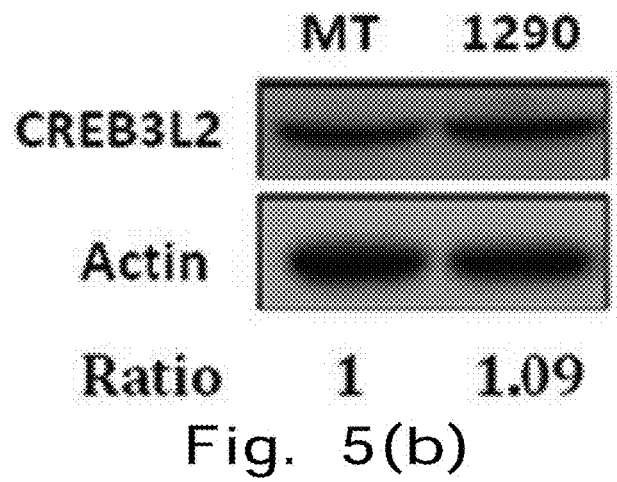
FIG. 5(b) shows the viral protein cAMP responsive element binding protein 3-like 2 (CREB3L2) expression in A549 cells transfected with hsa-miR-1290.
Figure 5C:
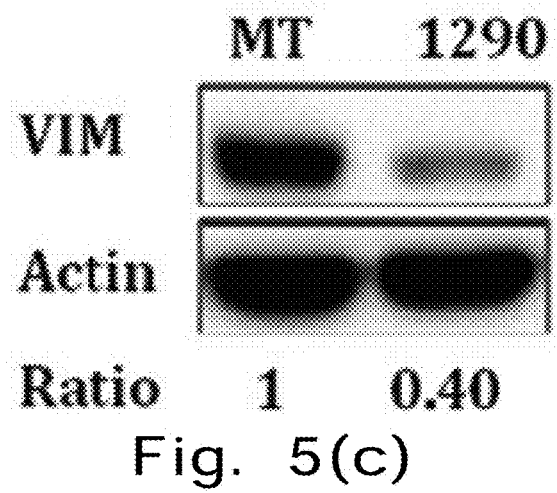
FIG. 5(c) shows the viral protein polymerase I and transcript release factor (PTRF) expression in A549 cells transfected with hsa-miR-1290.
Figure 5D:
FIG. 5(d) shows the viral protein Vimentin (VIM) expression in A549 cells transfected with hsa-miR-1290.
Figure 5E:
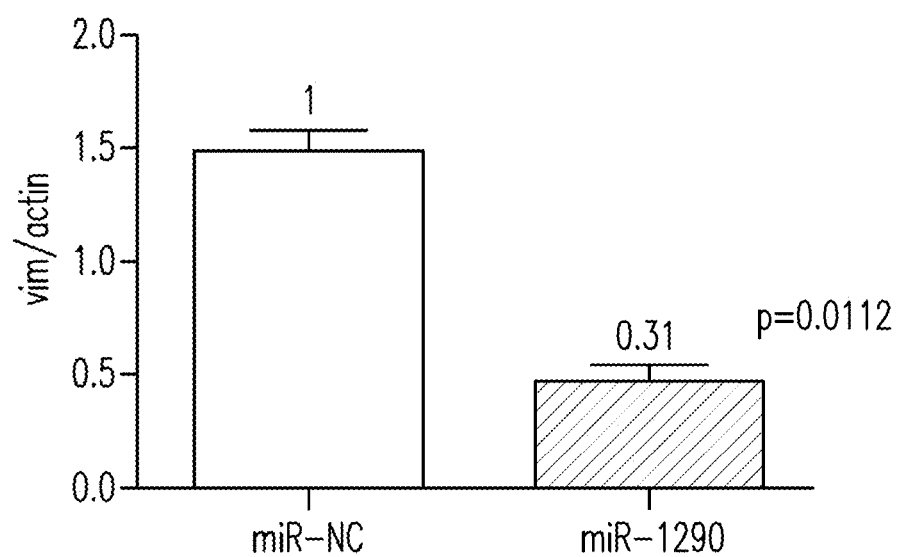
FIG. 5(e) shows the Vimentin mRNA expression in A549 cells transfected with hsa-miR-1290.
Figure 6A:
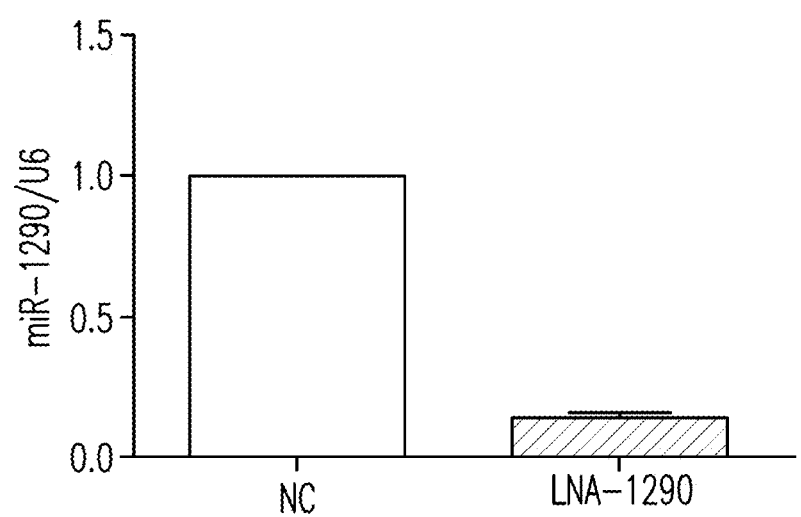
FIG. 6(a) shows the transfection efficiency of LNA-1290 in A549 cells.
Figure 6B:
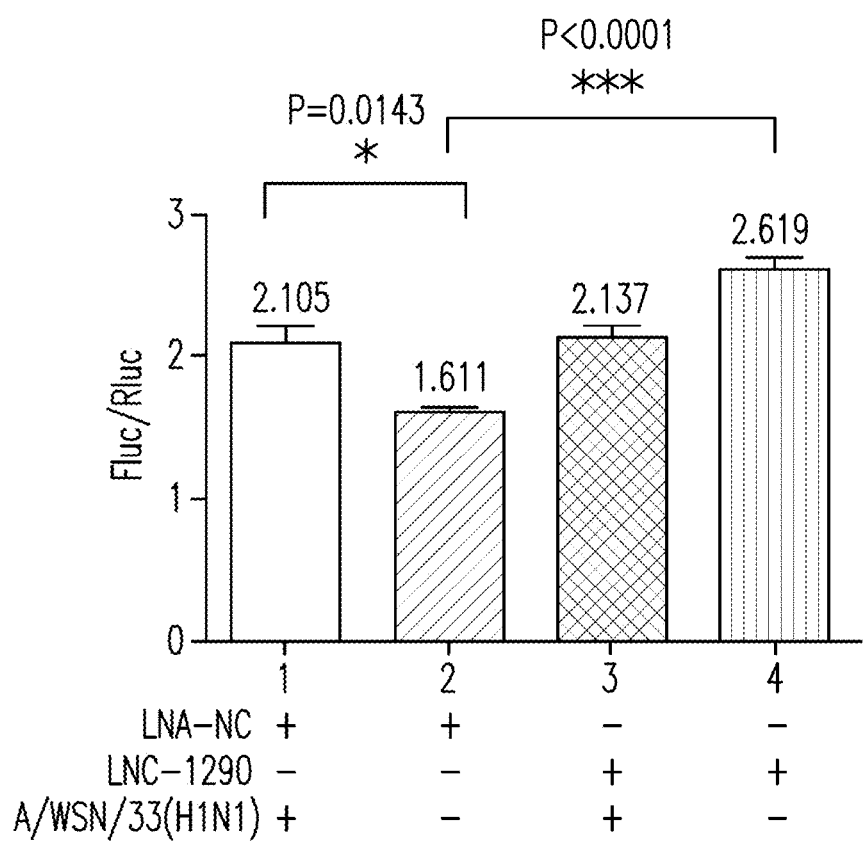
FIG. 6(b) shows human Vimentin-3'untranslated region (hVIM-3'UTR) expression in A549 cells transfected with LNA-1290.
Figure 7A:
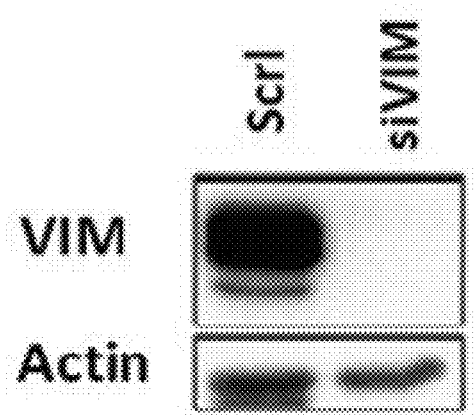
FIG. 7(a) shows the inhibition efficiency of Vimentin in A549 cells transfected with siVIM.
Figure 7B:
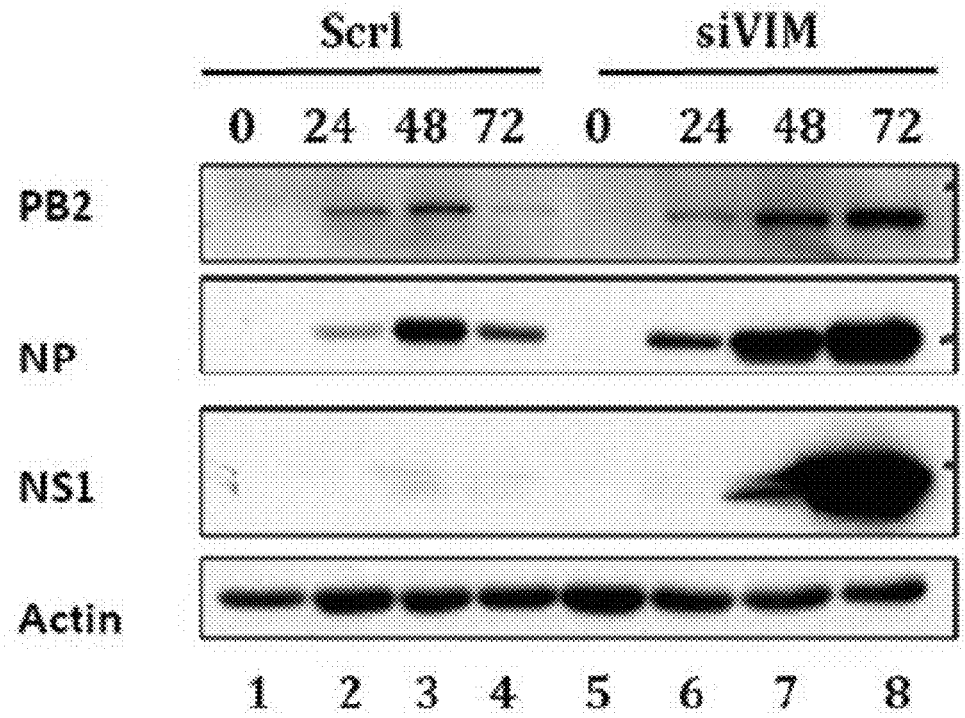
FIG. 7(b) shows the viral protein expression in A549 cells transfected with siVIM.
Figure 7C:
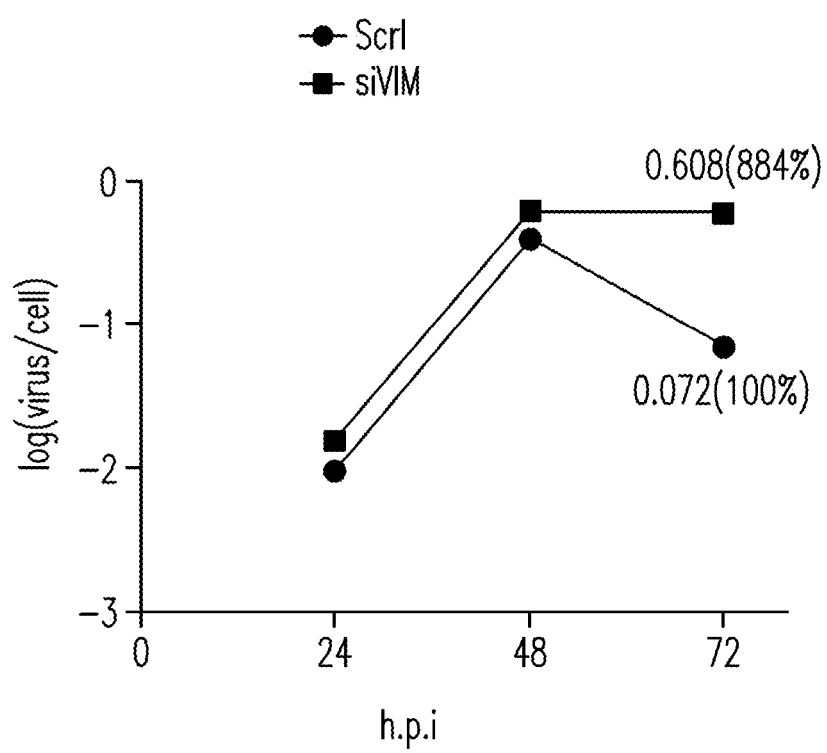
FIG. 7(c) shows the viral production of a single cell transfected with siVIM.

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

According to an embodiment of the present invention, a method of diagnosing Influenza A is disclosed. The method includes the step of determining a level of microRNA-1290 (miR-1290) in a cell of a subject based on a measurement of a level of an oligonucleotide complementary to a corresponding segment of the nucleotide sequence of miR-1290 (SEQ ID NO: 1), wherein at least one of the nucleotides in the oligonucleotide is Thymidine phosphate.

The virus subtypes of Influenza A may be H7N9, H1N1, H5N1, H1N2, H2N2, H2N3, H3N1, H3N2, H3N8, H5N2, H5N3, H5N8, H5N9, H7N1, H7N2, H7N3, H7N4, N7N7, H9N2, H10N7 or H10N8, preferably H1N1. The subject may be a human.

The oligonucleotide complementary to the corresponding segment of the nucleotide sequence of miR-1290 may be cDNA. The cDNA may be produced by reverse transcription using the miR-1290 as a template. The method may further include the step of amplifying the cDNA of the miR-1290 using polymerase chain reaction (PCR). The PCR may be real-time polymerase chain reaction (real-time PCR). The corresponding segment of the nucleotide sequence of miR-1290 may be the total or a part of SEQ ID NO: 1. The level of the oligonucleotide is proportional to the level of microRNA-1290. When the subject is infected with Influenza A, the level of microRNA-1290 significantly increases and consequently the level of the oligonucleotide also significantly increases. Thus, when a significant increase in the level of the oligonucleotide is measured, it can be diagnosed that the subject is infected with Influenza A.

According to an embodiment of the present invention, a method of treating Influenza A is disclosed. The method includes the step of administering a pharmaceutical composition including an oligonucleotide complementary to a corresponding segment of the nucleotide sequence of microRNA-1290 (miR-1290) (SEQ ID NO: 1) to a subject suffering from Influenza A, wherein at least one of the nucleotides in the oligonucleotide is Thymidine phosphate.

The pharmaceutical composition may be powder or liquid, and the pharmaceutical composition may be administered nasally. Some other miRNA inhibitors, such as miR-122 inhibitor, are administered via vascular injection and are thus easy to degrade. The pharmaceutical composition in the present invention has no such problem because it is administered nasally.

Today, most drugs for treating Influenza are against viral proteins. Viral proteins are prone to mutate, and thus it is easy for them to acquire drug resistance. The pharmaceutical composition in the present invention is against host cells. Host cells do not mutate easily, and thus the pharmaceutical composition in the present invention is unlikely to produce drug resistance.

The virus subtypes of Influenza A may be H7N9, H1N1, H5N1, H1N2, H2N2, H2N3, H3N1, H3N2, H3N8, H5N2, H5N3, H5N8, H5N9, H7N1, H7N2, H7N3, H7N4, N7N7, H9N2, H10N7 or H10N8, preferably H1N1. The subject may be a human.

The pharmaceutical composition can restore the expression of Vimentin, which is inhibited by miR-1290.

The nucleotides in the oligonucleotide may be independently selected from the group consisting of a DNA unit, an RNA unit, a LNA (locked nucleic acid) unit, a 2'-OMe DNA unit and a 2'-OMe RNA unit. At least one of the intemucleoside linkages between the nucleotides in the oligonucleotide may be a phosphorothioate intemucleoside linkage. The oligonucleotide may be 5'- or 3'-cholesteryl-oligonucleotide. Preferably, the oligonucleotide has the nucleotide sequence of SEQ ID NO: 2.

According to an embodiment of the present invention, a method of treating Influenza A is disclosed. The method includes the step of administering a pharmaceutical composition including an oligonucleotide complementary to a corresponding segment of the nucleotide sequence of microRNA-1290 (miR-1290) (SEQ ID NO: 1) to a subject suffering from Influenza A.

At least one of the nucleotides in the oligonucleotide is chemically modified. Chemical modification can make the oligonucleotide stable.

The pharmaceutical composition may be powder or liquid, and the pharmaceutical composition may be administered nasally.

The virus subtypes of Influenza A may be H7N9, H1N1, H5N1, H1N2, H2N2, H2N3, H3N1, H3N2, H3N8, H5N2, H5N3, H5N8, H5N9, H7N1, H7N2, H7N3, H7N4, N7N7, H9N2, H10N7 or H10N8, preferably H1N1. The subject may be a human.

The pharmaceutical composition can restore the expression of Vimentin, which is inhibited by miR-1290.

The nucleotides in the oligonucleotide may be independently selected from the group consisting of a DNA unit, an RNA unit, a LNA (locked nucleic acid) unit, a 2'-OMe DNA unit and a 2'-OMe RNA unit. At least one of the intemucleoside linkages between the nucleotides in the oligonucleotide may be a phosphorothioate intemucleoside linkage. The oligonucleotide may be 5'- or 3'-cholesteryl-oligonucleotide. Preferably, the oligonucleotide has the nucleotide sequence of SEQ ID NO: 2.

Experiments

1. Analyzing miRNA Expressions in A549 and DF-1 Cells after A/WSN/33 (H1N1) Infection by Micro Array Infect A549 and DF-1 cells with 0.001 MOI (multiplicity of infection) A/WSN/33 (H1N1) for 12, 24 and 36 hours or 2 MOI A/WSN/33 (H1N1) for 2, 6 and 10 hours, and then analyze miRNA expressions in A549 and DF-1 cells by microarray. As a result, both miRNA expressions in A549 and DF-1 cells are influenced by A/WSN/33 (H1N1) infection. Find the intersections of miRNAs whose expression levels, before and after infection, have a difference over 1.5 times and miRNAs having no homology with birds. As a result, 8 miRNAs and 12 miRNAs are screened with 0.001 MOI and 2 MOI.

2. Verifying Expression Levels of the Screened miRNAs after A/WSN/33 (H1N1) Infection by Real-Time Polymerase Chain Reaction (Real-Time PCR)

Infect A549 cells with 0.001 MOI or 2 MOI A/WSN/33 (H1N1), and extract total RNAs of A549 cells with Trizol (Invitrogen) for 12, 24 and 36 hours or 2, 6 and 10 hours, respectively. Take 500 ng of total RNA and synthesize cDNA with Superscript III Reverse Transcriptase (Invitrogen), take 1 μl cDNA to mix with SYBR Green Master Mix (KAPA), react at 16° C. for 30 minutes, react at 20° C. for 30 seconds, react at 42° C. for 30 seconds and react at 50° C. for 1 second, and then repeat 50 times to amplify the templates. Input the obtained Ct value into the Ct-number equation obtained by serial dilution of pre-miR-1290 (Ambion, Pre-miR™ miRNA Starter Kit), as shown in FIG. 1(a), so as to obtain the copy number of Homo sapiens miRNA-1290 (hsa-miR-1290). The results show that hsa-miR-1290 has 5.5 and 1.9 times differences after 24 and 2 hours infection with 0.001 MOI and 2 MOI, respectively, as shown in FIG. 1(b) and FIG. 1(c).

Figure 8:
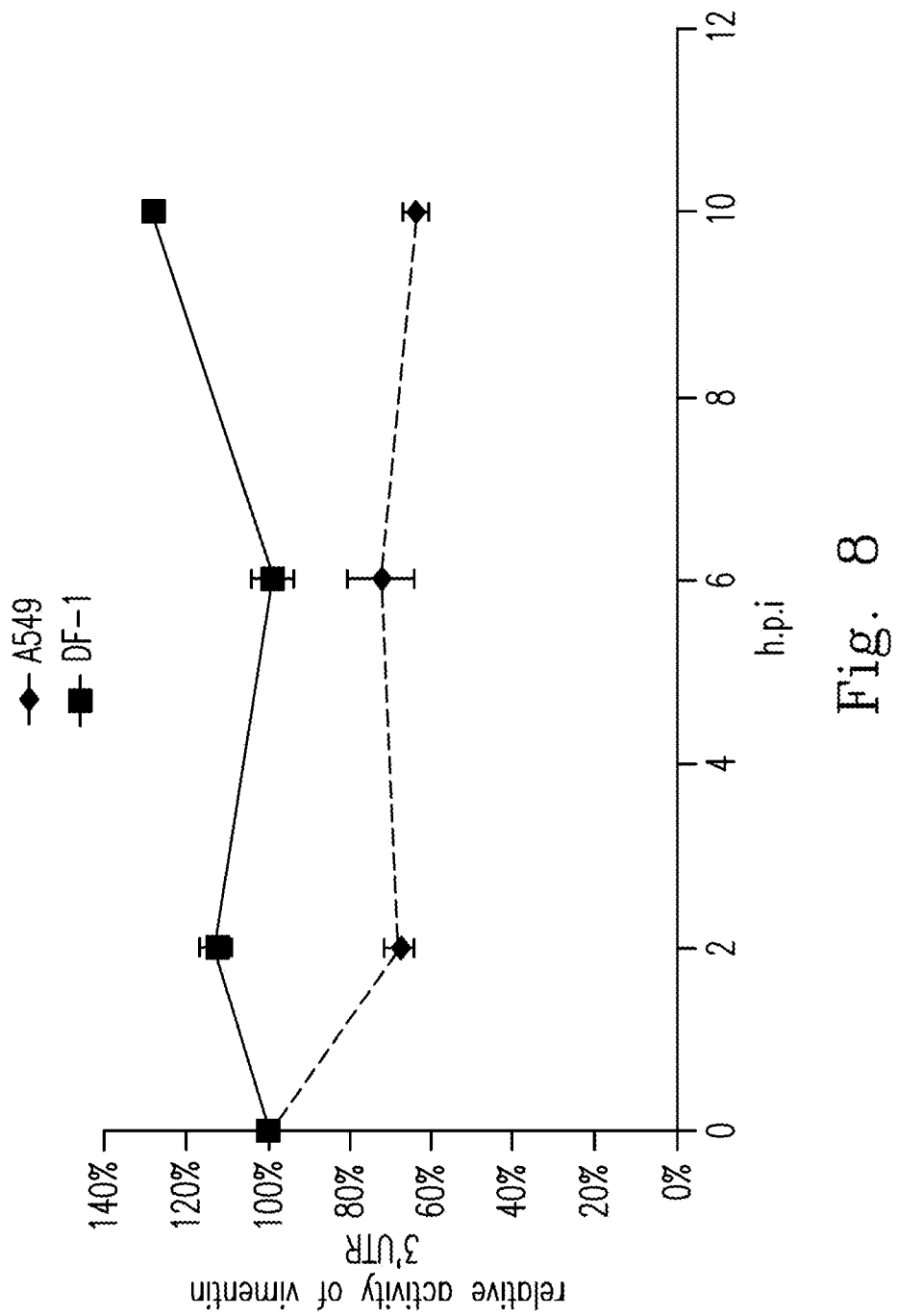
FIG. 8 shows human Vimentin-3'untranslated region (hVIM-3'UTR) and avian Vimentin-3' untranslated region (aVIM-3'UTR) expressions after A/WSN/33 (H1N1) infection in a single replication cycle.

3. Hsa-miR-1290 Expression in A549 Cells Increases Viral Production of A/WSN/33 (H1N1) in Multiple Replication Cycles Transfect 50 nM pre-miR negative control or 50 nM pre-miR-1290 into A549 cells with Lipofectamine RNAiMAX (Introgen), collect cells with Trypsin after one day, seed cells in a 12 well plate, and infect cells with 0.001 MOI A/WSN/33 (H1N1) for 24, 48 and 72 hours after 24 hours. Extract total RNAs on the fifth day, and analyze the transfection efficiency of hsa-miR-1290 by real-time PCR and inner standardizing data with U6, as shown in FIG. 2(*a*). Collect cells and supernatant at different infection time points. Analyze viral proteins with Western blot and using β-actin as the inner standard. Analyze viral expression with plaque assay. The results show that the expression of hsa-miR-1290 significantly increases the expression of viral proteins 48 and 72 hours after infection, as shown in FIG. 2(*b*). Viral production of a single cell transfected with hsa-miR-1290 is ten times larger than that of the negative control, as shown in FIG. 2(*c*).

4. Hsa-miR-1290 Expression in A549 Cells Increases Viral Production of A/WSN/33 (H1N1) in a Single Replication Cycle Transfect 50 nM pre-miR negative control or 50 nM pre-miR-1290 into A549 cells with Lipofectamine RNAiMAX (Introgen), collect cells with Trypsin after one day, seed cells in a 12 well plate, and infect cells with 2 MOI A/WSN/33 (H1N1) for 2, 6 and 10 hours after 24 hours. Extract total RNAs on the $58^{th}$ day, and analyze the transfection efficiency of hsa-miR-1290 by real-time PCR and inner standardizing data with U6, as shown in FIG. 3(*a*). Collect cells and supernatant at different infection time points. Analyze viral proteins with Western blot and using β-actin as the inner standard. Analyze viral expression with plaque assay. The results show that the expression of hsa-miR-1290 significantly increases the expression of viral proteins 10 hours after infection, as shown in FIG. 3(*b*). Viral production of a single cell transfected with hsa-miR-1290 also increases significantly 10 hours after infection, as shown in FIG. 3(*c*).

5. Locked Nucleic Acid miRNA 1290 (LNA-1290) Expression in A549 Cells Increases Viral Production of A/WSN/33 (H1N1) in Multiple Replication Cycles Transfect 50 nM LNA (locked nucleic acid) negative control (EXIQON) or 25 nM locked nucleic acid miRNA 1290 (LNA-1290) (EXIQON) into A549 cells with Lipofectamine RNAiMAX (Introgen), collect cells with Trypsin after one day, seed cells in a 12 well plate, and infect cells with 0.001 MOI A/WSN/33 (H1N1) for 24, 48 and 72 hours after 24 hours. Extract total RNAs on the fifth day, and analyze the transfection efficiency of LNA-1290 by real-time PCR and inner standardizing data with U6, as shown in FIG. 4(*a*). Collect cells and supernatant at different infection time points. Analyze viral proteins with Western blot and using β-actin as the inner standard. Analyze viral expression with plaque assay. The results show that compared to the negative control, the expression of LNA-1290 significantly decreases the expression of viral proteins 48 and 72 hours after infection, as shown in FIG. 4(*b*). Viral production also decreases by at least ten times after inhibiting the expression of hsa-miR-1290, as shown in FIG. 4(*c*).

6. Hsa-miR-1290 Expression in A549 Cells Inhibits Endogenous Vimentin Expression Use TargetScan and miRanda to predict target genes of hsa-miR-1290. As a result, cAMP responsive element binding protein 3-like 2 (CREB3L2), polymerase I and transcript release factor (PTRF) and Vimentin (VIM) are predicted. Transfect 50 nM pre-miR negative control or 50 nM pre-miR-1290 into A549 cells with Lipofectamine RNAiMAX (Introgen) for 72 hours. Extract total RNAs and proteins. Analyze the transfection efficiency of hsa-miR-1290 by real-time PCR and inner standardizing data with U6, as shown in FIG. 5(*a*). Take 30 μg total proteins to analyze target genes expression by Western blot and inner standardizing data with β-actin. Divide the value obtained by transfecting pre-miR-1290 by the value obtained by transfecting pre-miR negative control to obtain a ratio. Vimentin protein expression is suppressed to 40% by hsa-miR-1290, but CREB3L2 and PTRF protein expressions do not change significantly, as shown in FIGS. 5(*b*)-5(*d*). Vimentin mRNA expression is also suppressed to 30% by hsa-miR-1290, as shown in FIG. 5(*e*). The results show that hsa-miR-1290 can inhibit Vimentin expression by degrading mRNA.

7. LNA-1290 Expression in A549 Cells Restores Human Vimentin-3'Untranslated Region (hVIM-3'UTR) Degradation Transfect pMIR-Fluc-hVIM-3'UTR and pRL-TK into A549 cells for 12 hours, and then transfect 25 nM LNA-1290 into A549 cells for 12 hours. Infect cells with 2 MOI A/WSN/33 (H1N1) for 6 hours. Extract total RNA, and analyze the transfection efficiency of LNA-1290 by real-time PCR and inner standardizing data with U6, as shown in FIG. 6(*a*). Analyze expression levels of Firefly luciferase (Fluc) and *Renilla* luciferase (Rluc) with dual-luciferase reporter assay (Promega) to obtain a Fluc/Rluc value. As a result, the expression of human Vimentin-3'untranslated region (hVIM-3'UTR) decreases by about 25% after infecting cells with A/WSN/33 (H1N1). However, if LNA-1290 is expressed before the infection, the suppressed hVIM-3'UTR is restored, as shown in FIG. 6(*b*). The result shows the inhibition specificity of hsa-miR-1290 to Vimentin.

8. Inhibiting Vimentin Expression Increases Viral Production of A/WSN/33 (H1N1) in A549 Cells in Multiple Replication Cycles Transfect 60 pmole siVIM (Ambion) or Scrl (GeneDirex) into A549 cells with Lipofectamine RNAiMAX (Introgen), collect cells with Trypsin after 24 hours, seed cells in a 12 well plate, and infect cells with 0.001 MOI A/WSN/33 (H1N1) for 24, 48 and 72 hours after 24 hours. Extract total RNAs on the fifth day, and take 30 μg total proteins to monitor the inhibition efficiency of Vimentin, as shown in FIG. 7(*a*). Analyze viral proteins with Western blot and using β-actin as the inner standard. Analyze viral expression with plaque assay. As a result, compared to the control, viral proteins increase significantly 72 hours after infection when inhibiting Vimentin expression, and viral expression level increases 10 times 72 hours after infection, as shown in FIGS. 7(*b*)-7(*c*). Inhibiting Vimentin expression and expressing has-miR-1290 both positively regulate A/WSN/33 (H1N1) replication. This further shows that Vimentin and has-miR-1290 regulate A/WSN/33 (H1N1) on the same pathway.

9. Human Vimentin-3'Untranslated Region (hVIM-3'UTR) and Avian Vimentin-3'Untranslated Region (aVIM-3'UTR) Expressions after A/WSN/33 (H1N1) Infection in a Single Replication Cycle Co-transfect pMIR-hVIM-3'UTR-Fluc or pMIR-aVIM-3'UTR-Fluc into A549 or DF-1 cells for 24 hours, and infect cells with 2 MOI A/WSN/33 (H1N1) for 2, 6 and 10 hours. Analyze expression levels of Firefly luciferase (Fluc) and *Renilla* luciferase (Rluc) with dual-luciferase reporter assay (Promega) to obtain a Fluc/Rluc value. After obtaining the Fluc/Rluc value, divide the Fluc/Rluc value obtained by an infected sample by the Fluc/Rluc value obtained by an uninfected sample. The results show that hVIM-3'UTR expression in A549 cells decreases to 60%-80% after infection. aVIM-3'UTR expression in DF-1 cells increases to 120%440% after infection, as shown in FIG. 8. A/WSN/33 (H1N1) indeed only inhibits Vimentin expression in A549 cells, and regulates Vimentin expression with species specificity.

Embodiments

1. A method of diagnosing Influenza A, comprising the step of determining a level of microRNA-1290 (miR-1290) in a cell of a subject based on a measurement of a level of an oligonucleotide complementary to a corresponding segment of the nucleotide sequence of miR-1290 (SEQ ID NO: 1), wherein at least one of the nucleotides in the oligonucleotide is Thymidine phosphate.
2. The method of Embodiment 1, wherein the oligonucleotide is cDNA produced by reverse transcription using the miR-1290 as a template.
3. The method of Embodiments 1-2, further comprising the step of amplifying the cDNA of the miR-1290 using polymerase chain reaction (PCR).
4. The method of Embodiments 1-3, wherein the Influenza A is caused by a H1N1 virus.
5. The method of Embodiments 1-4, wherein the subject is a human.
6. A method of treating Influenza A, comprising the step of administering a pharmaceutical composition including an oligonucleotide complementary to a corresponding segment of the nucleotide sequence of microRNA-1290 (miR-1290) (SEQ ID NO: 1) to a subject suffering from Influenza A, wherein at least one of the nucleotides in the oligonucleotide is Thymidine phosphate.
7. The method of Embodiment 6, wherein the pharmaceutical composition is administered nasally.
8. The method of Embodiments 6-7, wherein the pharmaceutical composition reduces H1N1 viral production.
9. The method of Embodiments 6-8, wherein the pharmaceutical composition restores the expression of Vimentin.
10. The method of Embodiments 6-9, wherein the subject is a human.
11. The method of Embodiments 6-10, wherein the nucleotides in the oligonucleotide are independently selected from the group consisting of a DNA unit, an RNA unit, a LNA (locked nucleic acid) unit, a 2'-OMe DNA unit and a 2'-OMe RNA unit.
12. The method of Embodiments 6-11, wherein at least one of the internucleoside linkages between the nucleotides in the oligonucleotide is a phosphorothioate internucleoside linkage.
13. The method of Embodiments 6-12, wherein the oligonucleotide is 5'- or 3'-cholesteryl-oligonucleotide.
14. The method of Embodiments 6-13, wherein the oligonucleotide has the nucleotide sequence of SEQ ID NO: 2.
15. A method of treating Influenza A, comprising the step of administering a pharmaceutical composition including an oligonucleotide complementary to a corresponding segment of the nucleotide sequence of microRNA-1290 (miR-1290) (SEQ ID NO: 1) to a subject suffering from Influenza A.
16. The method of Embodiment 15, wherein at least one of the nucleotides in the oligonucleotide is chemically modified.
17. The method of Embodiments 15-16, wherein the pharmaceutical composition reduces H1N1 viral production.
18. The method of Embodiment 15-17, wherein the pharmaceutical composition restores the expression of Vimentin.
19. The method of Embodiment 15-18, wherein the nucleotides in the oligonucleotide are independently selected from the group consisting of a DNA unit, an RNA unit, a LNA (locked nucleic acid) unit, a 2'-OMe DNA unit and a 2'-OMe RNA unit.
20. The method of Embodiment 15-19, wherein at least one of the internucleoside linkages between the nucleotides in the oligonucleotide is a phosphorothioate internucleoside linkage.

What is claimed is:

1. A method of treating Influenza A, comprising the step of administering a pharmaceutical composition including an oligonucleotide complementary to a corresponding segment of the nucleotide sequence of microRNA-1290 (miR-1290) (SEQ ID NO: 1) to a subject suffering from Influenza A, wherein at least one of the nucleotides in the oligonucleotide is Thymidine phosphate.

2. The method according to claim 1, wherein the pharmaceutical composition is administered nasally.

3. The method according to claim 1, wherein the subject is suffering from H1N1 and the pharmaceutical composition reduces H1N1 viral production.

4. The method according to claim 1, wherein the pharmaceutical composition restores the expression of Vimentin.

5. The method according to claim 1, wherein the subject is a human.

6. The method according to claim 1, wherein the nucleotides in the oligonucleotide are independently selected from the group consisting of a DNA unit, an RNA unit, a LNA (locked nucleic acid) unit, a 2'-OMe DNA unit and a 2'-OMe RNA unit.

7. The method according to claim 1, wherein at least one of the internucleoside linkages between the nucleotides in the oligonucleotide is a phosphorothioate internucleoside linkage.

8. The method according to claim 1, wherein the oligonucleotide is 5'- or 3'-cholesteryl-oligonucleotide.

9. The method according to claim 1, wherein the oligonucleotide has the nucleotide sequence of SEQ ID NO: 2.

10. A method of treating Influenza A, comprising the step of administering a pharmaceutical composition including an oligonucleotide complementary to a corresponding segment of the nucleotide sequence of microRNA-1290 (miR-1290) (SEQ ID NO: 1) to a subject suffering from Influenza A.

11. The method according to claim 10, wherein at least one of the nucleotides in the oligonucleotide is chemically modified.

12. The method according to claim 10, wherein the subject is suffering from H1N1 and the pharmaceutical composition reduces H1N1 viral production.

13. The method according to claim 10, wherein the pharmaceutical composition restores the expression of Vimentin.

14. The method according to claim 10, wherein the nucleotides in the oligonucleotide are independently selected from the group consisting of a DNA unit, an RNA unit, a LNA (locked nucleic acid) unit, a 2'-OMe DNA unit and a 2'-OMe RNA unit.

15. The method according to claim 10, wherein at least one of the internucleoside linkages between the nucleotides in the oligonucleotide is a phosphorothioate internucleoside linkage.

* * * * *